United States Patent [19]
Torabinejad et al.

[11] Patent Number: 5,415,547
[45] Date of Patent: May 16, 1995

[54] TOOTH FILLING MATERIAL AND METHOD OF USE

[75] Inventors: Mahmoud Torabinejad, Loma Linda; Dean J. White, San Dimas, both of Calif.

[73] Assignee: Loma Linda University, Loma Linda, Calif.

[21] Appl. No.: 52,411

[22] Filed: Apr. 23, 1993

[51] Int. Cl.$^6$ .............................................. A61C 5/00
[52] U.S. Cl. ................................... 433/228.1; 433/224
[58] Field of Search ................. 433/228.1, 224; 106/35

[56] References Cited

U.S. PATENT DOCUMENTS

| | | | |
|---|---|---|---|
| 3,973,972 | 8/1976 | Muller | 433/228.1 |
| 4,171,544 | 10/1979 | Hench et al. | 433/180 |
| 4,337,186 | 6/1982 | Crisp et al. | 525/362 |
| 4,376,835 | 3/1983 | Schmitt et al. | 433/228.1 |
| 4,557,691 | 12/1985 | Martin et al. | 433/228.1 |
| 5,236,362 | 8/1993 | Cohen et al. | 433/228.1 |

OTHER PUBLICATIONS

The Adaption and Sealing Ability of Light-Cured Glass Ionomer Retrograde Root Fillings, International Endodontic Journal (1991) 24, pp. 223-232.

Sealing Ability of Dental Amalgams as Retrograde Fillings in Endodontic Therapy, Journal of Endodontics, Dec. 1983, vol. 9, No. 12, pp. 551-553.

The Apical Seal Via the Retrosurgical Approach, Oral Surg., Aug. 1982, pp. 213-218.

Apical Leakage Associated with Retrofilling Techniques: A Dye Study, Journal of Endodontics, Aug. 1986, vol. 12, No. 8, pp. 331-336.

Primary Examiner—Cary E. O'Connor
Attorney, Agent, or Firm—Knobbe Martens Olson & Bear

[57] ABSTRACT

An improved method for filing and sealing tooth cavities involves the use of a cement composition which exhibits several advantages over existing orthograde and retrograde filling materials, including the ability to set in an aqueous environment. In a preferred embodiment, the cement composition comprises Portland cement, or variations in the composition of such cement, which exhibit favorable physical attributes sufficient to form an effective seal against reentrance of infectious organisms.

10 Claims, 3 Drawing Sheets

TOOTH FILLING MATERIAL AND METHOD OF USE

FIELD OF THE INVENTION

The present invention relates to an improved method of treating and filling cavities in teeth caused by decay, and, more particularly, to a method for sealing the treated cavity or root canal to prevent infiltration of infectious bacteria into the living tissues of the tooth.

BACKGROUND OF THE INVENTION

Hard tissues of the anatomy are often subject to damage or degradation, which require repair and reconstruction. In the case of teeth, dental decay is one of the most common type of disorders. It is typically caused by the bacteria which are commonly present in the mouth. Although the mechanism by which bacteria cause decay is not completely understood, it is believed that cariogenic organisms, by using sucrose, and to a lesser extent other sugars, produce polymers which bind the organisms to the tooth surface and acids which cause the demineralization resulting in cavity formation.

The decay of bones and especially teeth is referred to as "caries," and the resulting cavity forms a carious lesion in the tooth. Depending upon the degree of advance state of such decay, it may affect the various parts of a tooth, the principal components being the enamel, the dentin, the pulp, and the cementum.

The enamel of a tooth is the intensely hard calcareous (i.e., calcium based) substance that forms a thin layer which caps or partly covers the teeth of most mammals, including humans and other vertebrates. The enamel is the hardest substance of the animal body and its strength allows a tooth to perform its laborious function over many years of life of most humans. The hardness of the enamel also serves to protect the sensitive living tissue within.

The dentin also comprises calcareous material similar to bone but harder. The dentin is a living tissue comprised of a matrix of minute tubules which enter into the inner cavity of the tooth where the living tissues thereof are housed. The "pulp" of the tooth comprises the living or viable tissues of the tooth which are contained within the pulp cavity. The pulp cavity comprises the pulp chamber, located near the crown of the tooth, and the root canal, which extends down to the very proximal or periapical regions of the tooth. The pulp is comprised of connective tissue, blood vessels which nourish the tooth, and nerves which transmit pain and other signals to the brain. The blood vessels and nerves enter the tooth at the tip or apical section of the root canal. Depending upon the type of tooth, there is significant circulation of living matter within the pulp of the tooth.

The cementum is a thin, fairly hard bone tissue covering the root of the tooth. Surrounding the cementum is the periodontal ligament which serves to mount the tooth in the bony socket or alveolus which is formed in the alveolar bone or jaw bone in which the teeth are set.

Dental decay is most likely to affect the enamel, dentin and/or pulp. Once dental caries is found in the enamel, the typical therapy is to remove it in order to prevent further penetration of the decay into the tooth. Such penetration could spread infection throughout the mouth and the body, and possibly result in loss of the tooth. Such therapy for cavities formed by decay is typically referred to as a "filling." In accordance with this well-known procedure, a dentist or other authorized practitioner drills out the cavity formed by the decaying material and may also form undercuts in order to secure the filling material. The dentist then fills the cavity with a filling material which replaces the portion of the tooth lost to decay. This filling material is placed downward into the tooth from the upper or crown regions of the tooth, and is typically referred to as an "orthograde" filling. The dentist then packs the filling material densely and shapes it appropriately.

Once a carious lesion penetrates the enamel and enters the dentin, the viable tooth processes are affected and the tooth may become painful. At this stage, the infectious organisms have relatively ready access to the pulp. Thus, there is a likelihood of formation of abscesses indicated by swelling, pus and sometimes severe pain. The abscesses are typically formed in the periapical tissues surrounding the apex or apical section of the tooth where it intersects the alveolar bone. At this stage of the disease, the tooth can be treated successfully by root canal therapy. In this process, access to the pulp is achieved by drilling whereupon the dead or decayed pulp is removed by the use of small files. The pulp chamber, including the root canal, is then filled or obturated with an inert filling material in order to prevent, ideally, the return of infectious organisms from the mouth to the living periapical tissues surrounding the root tip.

Root canal therapy is not always completely successful. It is estimated that in about 20–30% of the cases, despite the obturation of the root canal by filling material, infection returns. This is usually caused by the migration of bacteria and other infectious organisms from the mouth along the root canal cavity. The bacteria migrates through the interstices of the canal to the living periapical tissues which remain following the root canal therapy. Furthermore, the root canal system is complex and cannot always be completely cleaned with the present techniques and instruments. Thus, periapical abscesses may again form at the tip of the root canal. In these cases, the interstitial seal between the orthograde filling material and the walls of the root canal is not sufficient to prevent the invasion of infectious matter.

Retreatment of unsuccessful root canal cases is the preferred therapy, and it usually results in a successful outcome. However, when non-surgical attempts prove unsuccessful or are impossible, a surgical method known as "apicoectomy" is available. Under this procedure, the patient is placed under a suitable anesthesia and the gums are surgically cut to expose the infected tooth apex. The apex of the tooth is then removed and the resected root end is prepared. Finally, a "retrograde" filling material is inserted into the exposed cavity at the root tip in order to, hopefully, seal the root canal and prevent the migration of oral bacteria into the living periapical tissues. Clearly, this apicoectomy is a painful and expensive procedure. It could be avoided through the use of cavity-filling materials which form effective seals against the migration of infectious organisms.

Various materials have been used to fill teeth. Amalgam is the most common filling material, but others have also been used.

A tooth filling material must exhibit various qualities. It must exhibit good adherence and adaptability to the tooth walls of the cavity. It must be compatible with the surrounding tissue, and must not cause staining or other adverse effects to the surrounding tooth structure. It must harden to provide structural support for the tooth, including its biting surface. It must be relatively easy to apply in what is sometimes a difficult environment due to blood, moisture and potential access problems. It is also important for diagnostic purposes that a filling material be radiopaque, i.e., exhibit a high absorption of the short wavelength x-ray radiation utilized in dental diagnostics. It should also be sterile or easily sterilized.

When filling tooth cavities, it is important to keep the fluid and bacteria present in the mouth from reentering the cavity and causing further decay. Thus, the chosen filling material must adequately seal the cavity to prevent the migration of such fluid and bacteria into the cavity. As noted above, this sealing ability of the filling material is particularly important when the decay has caused access to the pulp of the tooth.

As with conventional fillings and root canals, various materials have been suggested as retrograde filling materials. An ideal retrograde filling material should have many of the same qualities desired in an orthograde filling material. It should adhere and adapt to the dentinal walls of the root end preparations, should prevent leakage of microorganisms and their byproducts into the periapical tissues and should be biocompatible with the periapical tissues. It should also be insoluble in tissue fluids, dimensionally stable, and unsusceptible to the presence of moisture. Additionally, any antimicrobial qualities are beneficial, and would further inhibit infection and abscess.

The types of materials which have been suggested as retrofilling materials consist of many of the standard orthograde dental filling materials, and include gutta percha, zinc oxide eugenol paste, cavity, composite resins, gold foil, glass ionomers, standard amalgams and other materials. The suitability of these materials as retrograde filling materials have been tested by their sealing ability, marginal adaption to the dentinal walls, biocompatibility and their clinical performance. To date, no material has been found which satisfies all the desired properties of a retrofilling material.

For example, amalgam has been the most commonly used retrograde filling material for many years, even though it has many disadvantages. One of its primary disadvantages is the allowance of initial leakage. When initially applied the amalgam has poor adaption to the dentinal cavity walls and allows leakage between the interface of the amalgam and dentinal walls. This leakage reduces over time due to secondary corrosion as the interface is exposed to the oral fluids. Even with secondary corrosion, the effectiveness of the seal has been questioned, and the corrosion products in the gap between the amalgam and the cavity walls may themselves be detrimental. Additional disadvantages of amalgam include (a) mercury and lead contamination; (b) non-sterility; (c) moisture sensitivity; (d) need for an undercut in the cavity preparation; (e) staining of hard and soft tissues; (f) scatter of amalgam particles; and (g) the need to apply a cavity varnish to the dentinal walls to limit initial leakage.

Because of these disadvantages of amalgam, zinc oxide eugenol ("ZOE") based cements such as Super EBA and IRM have also been used as retrograde filling materials. The disadvantages of ZOE-based cements include: (a) moisture sensitivity; (b) irritation of vital tissue; (c) solubility; (d) need for an undercut in the cavity preparation; and (e) difficulty in clinical handling of the material.

Thus, a need exists for a material to repair and reconstruct hard tissue of the anatomy, and more particularly a need exists for an improved dental filling and sealing material which can be applied in either an orthograde or retrograde cavity. It should satisfy all or most of the ideal characteristics of such filling materials. Namely, it should provide an improved seal at the surface of the tooth structure and the cavity thereby preventing the migration of bacteria and material into the cavity or periapical tissues. The filling material should also be easily applied, able to form a structurally solid filling, be biocompatible, be compatible with the presence of moisture, and easily sterilized.

SUMMARY OF THE INVENTION

The present invention comprises a novel method for treating, filling and sealing cavities in teeth in which the filling material satisfies the existing need by providing an improved seal against invading bacteria. The present method has both human and veterinarian applications. The method utilizes a cement composition in which, in a preferred embodiment, the principal component is Portland cement. In other embodiments, the cement composition of the present method is comprised of cement composition which are similar to those of Portland cement and in which the composition has certain physical characteristics.

This novel use for a cement composition provides many advantages over prior dental filling and sealing materials. In the preferred embodiment, Portland cement sets in the presence of moisture and blood, and is therefore easily applied and suitable for use in moist environments such as the mouth. This is particularly important when used as a retrograde filling material where fluid and blood are often difficult to control.

Although Portland cement is not radiopaque itself, an additive can be used in conjunction with the Portland cement to render the overall cement composition radiopaque. The cement composition utilized in the present invention is also compatible with surrounding tissue. This is particularly important when it is in direct contact with the periapical tissues, for example, when used as a retrograde filling material.

The cement composition is easily sterilized. It can be gas sterilized and, unlike amalgam, can also be autoclaved. The cement composition also has antimicrobial qualities which may further reduce the possibility of infection or further decay of the tooth structure.

The cement composition is also easily prepared and may be applied using standard dental instruments. In addition to its superior sealing ability, the present cement composition has several advantages over existing filling materials in terms of its usage. First, it is easy to mix and place into the cavity preparation with a small amalgam carrier. Second, as noted above, it is not essential that it be used in a dry field. Third, when excess material occurs during insertion, it is easy to remove. Fourth, the material does not contract upon setting, thus demonstrating good conformance with the cavity walls. The hardened cement composition may also later be removed by standard dental techniques and it therefore can be used as a temporary filler or sealant during endodontic therapy.

Due to the presence of blood and moisture, the mouth is a less than ideal environment for many materials which could otherwise be useful as dental filling and sealing materials. For example, typical amalgams are sensitive to moisture and set less than adequately if care is not taken to minimize moisture. Not only is the cement of the present invention not adversely affected by moisture in the mouth, but such moisture actually plays an important role in the hydration reactions responsible for the hardening and sealing process.

A significant advantage of the cement composition is its good adaption to dentinal walls and improved sealing ability. Based on a common dye penetration method of measuring the effectiveness of the seal, the cement composition of the preferred embodiment of the invention outperforms both amalgam and ZOE based cements which are currently used in practice.

The utilization of the cement composition can be used to seal cavities in a wide variety of situations. Often, the decay of a tooth is not so great as to require root canal therapy. In such cases, the cement composition can be used as a base to seal the cavity and/or pulp of the tooth.

In molar teeth the cavity may penetrate the pulp and result in an abscess of the alveolar bone. Although such a cavity does not involve the entire root canal, the cavity would eventually destroy the entire tooth if not properly sealed. The present cement composition may be used to seal the cavity and the remaining pulp, i.e., as a pulp capping agent. In other instances, where decay has not affected the pulp of the tooth, the cement composition may be used at the bottom of the cavity. In such a situation the cement acts as a liner to prevent further decay of the tooth.

Where the decay is so great as to require root canal therapy, the cement composition of the invention can be used to seal the root canal. In the cases where root canal therapy is not successful and surgical apicoectomy is required, the cement composition may be used as a retrograde filling material to form an apical seal, thus sealing the root canal from the periapical tissues.

Additionally, in case of root perforation(s), the cement can effectively fill the perforation and seal the avenue of communication between the oral cavity and the underlying bone. For example, in a two- or three-root molar, the fork in the roots forms, at the juncture, a "furcation." Thus, perforations in the furcation provide ready access to the tissues of the gum by oral bacteria.

The practitioner, however, will realize that these applications are only examples, and that the cement composition of the present invention can be utilized in a variety of dental situations which may require a filling or sealing material. In addition, in carrying out the method of the present invention, a wide variety of cement compositions having various physical attributes may be used effectively. For example, it is well-known that the specific composition of Portland cement will vary from location to location, depending upon the specific geographic location where it is made. It is believed that many such variations of Portland cement, and modified compositions thereof, can be effectively utilized in connection with the present method. In this regard, the cement composition must be clinically satisfactory, to the extent that the patient is comfortable and free of pain for an extended period of time, such as four to five years. In addition, the composition must be radiologically satisfactory and histologically satisfactory. In other words, the composition must not permit, in actuality, whether or not detected by the pain or discomfort of the patient, any infection or bone resorption. Furthermore, the composition must not cause rejection, inflammation or other allergic reaction on the part of the patient.

Thus, in light of the tests that have been conducted in connection with the cement composition contemplated by the present method, it is believed that various compositions could be successfully utilized. Another aspect of the present invention is the physical characteristics of the cement composition. The most important characteristic is the particle size or granulation of the cement. The particle size of Portland cement is usually expressed in Blaine number. Again, a cement composition having a range of Blaine numbers is believed to be effective in connection with the present method.

DETAILED DESCRIPTION OF THE PREFERRED EMBODIMENTS

Figure 1:
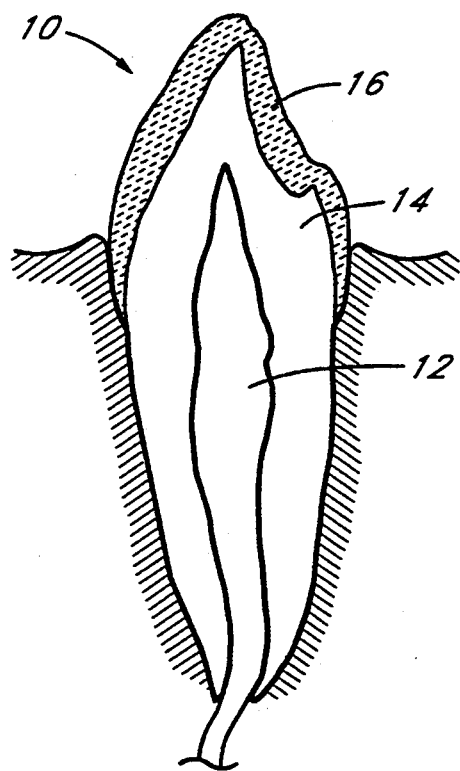
FIG. 1 is a longitudinal section of a healthy single-rooted tooth.

As noted above, the method of the present invention involves the use of cementitious filling materials to form an improved seal against migration of bacteria. This method provides a superior therapy for cavities found in the teeth of mammals, including humans, as well as other vertebrates. In another preferred embodiment, the cement composition contemplated by the present method comprises a Portland cement having a Blaine number falling within a certain range. However, the present invention is not limited to use of Portland cement or any particular composition thereof.

Thus, the principal component of the present cement composition by weight is calcium, which is present in the form of calcium oxide (CaO) on an average of about 65 weight percent. On the other hand, it is believed that a range of cement compositions having a calcium component is compatible with the present method wherein the calcium component is present by weight in an amount of about 50–75%.

Another important component of the present composition by weight is silicon, which is present in the form of silicon dioxide ($SiO_2$) in an average of about 21 weight percent. Again, it is believed that a suitable range for this component within the present cement composition is about 15–25 weight percent. In addition, the combination of the above calcium and silicon components is present on an average of about 86 weight percent. It appears that an acceptable range for these two components of the present cement composition is 70–95 weight percent.

Although not all of the cement compositions falling within these ranges had been utilized in test involving the present method, it is believed that such cement compositions could be effectively utilized.

Typically Portland cement is combined with aggregate and water to form concrete. The cement and water coat and bind to the aggregate, filling the spaces between the aggregate particles to form a ceramic composite material. The cement composition of the present invention, however, does not require the use of aggregate, but utilizes Portland cement with water.

The process of making Portland cement is well known and it can be purchased from any number of manufacturers under various trade names. The basic raw materials for Portland cement are lime (CaO), silica ($SiO_2$), alumina ($Al_2O_3$) and iron oxide ($Fe_2O_3$). These components are appropriately proportioned to produce various types of Portland cement.

In manufacturing Portland cement, the selected raw materials are crushed, ground, and proportioned for the desired composition then blended. The mixture is then fed into a rotary kiln where it is heated to temperatures of up to 1400°–1650° C. In this process the mixture is chemically converted to cement clinker which is subsequently cooled and pulverized. A small amount of gypsum ($CaSO_4.2H_2O$) is added to the cement to control the setting time of the concrete. The resulting cement consists principally of tricalcium silicate ($3CaO.SiO_2$), dicalcium silicate ($2CaO.SiO_2$), tricalcium aluminate ($3CaO.Al_2O_3$), and tetracalcium aluminoferrite ($4CaO.Al_2O_3.Fe_2O_3$). Calcium oxide is thus the principal component of Portland cement and typically comprises in excess of 60% by weight of the overall composition.

In general, as defined for its typical use, there are five basic types of Portland cement. These are identified by the standard specifications promulgated by the American Society for Testing of Materials (ASTM).

Type I is called normal Portland cement and is a general purpose cement suitable for all uses when the special properties of the other types are not required. Type I Portland cement is more generally available than are the other types of cement. Type I, or ordinary, Portland cement is typically used in assorted construction applications. In its normal applications, a Type I cement is used when the concrete is not subject to special sulphite hazard or where the heat generated by the hydration of the cement will not cause an objectionable rise in temperature.

Such conditions are typical of the mouth, which would normally not necessitate the use of ASTM Types II through V. Thus, the cement composition utilized of the present invention requires none of the special properties of Type II–V cements, and the preferred embodiment comprises an ASTM Type I Portland cement, although it is believed that such other types are within the scope of the invention as being suitable for the purposes described herein.

Of course, the practitioner will recognize in certain circumstances that the special characteristics of other ASTM types may be desirable. Type II cements are used when the cement will be exposed to moderate sulfite attacks, and where a moderate heat of hydration is desired because the cement is being used in a large structure, and may be subject to cracking due to uneven cooling. Type III Portland cement is used when early strength is desired, which may be suitable for certain applications where early strength may be advantageous. Type IV is a low heat of hydration cement useful when the heat of hydration is critical, for example, in extremely large structures such as dams. It would typically not be required in anatomical structures, but it may be criteria, for example, if an additive were used that may be adversely affected by a higher heat of hydration. Type V is a sulfite resistant cement useful when the cement is exposed to high sulfite attack.

The preferred embodiment of the present invention utilizes a Type I Portland cement having the following approximate composition:

| Component | Percentage |
| --- | --- |
| $SiO_2$ | 21% |
| $Al_2O_3$ | 4% |
| $Fe_2O_3$ | 5% |
| CaO | 65% |
| MgO | 2% |
| $SO_3$ | 2.5% |
| Alkalies ($Na_2O$, $K_2O$) | 0.5% |

This preferred Portland cement is commercially available as the Colton Fast-Set brand of the California Portland Cement Company.

The suitability of a particular cement composition for a given purpose is typically determined by a combination of its chemical composition and its physical attributes, i.e. the manner and degree to which the cement is ground (granulation) and the resulting particle size. The fineness of a cement is indicated by the cement's Blaine number, which represents the ratio of the cement's particle surface area to its weight (square centimeters of surface per gram). Portland cements generally have a Blaine number in the range of 3,200 to 5,500 $cm^2/g$ or greater. Faster setting cements, like that preferably utilized in the present invention, have a Blaine number in the range of 4,000–5,500 $cm^2/g$. The most preferable cement utilized in the present invention has a Blaine number in the range of 4,500–4,600 $cm^2/g$.

In this formulation, the cement composition comprises a powder consisting of fine particles which are hydrophilic and which set in the presence of moisture. Hydration of the powder results in a colloidal gel which solidifies to a hard rock-like substructure in less than four hours. The characteristics of the cement composition depend upon the size of the particles, the powder-water ratio, temperature, presence of water, and entrained air. After setting, the composition has compressive strength equal to that of amalgam.

Portland cement is combined with water to form the cement composition of the present invention. Depending on the particular application, various amounts of water may be utilized to form the cement composition. Enough water is added to the cement to give it a putty consistency, which then solidifies to a rock-like hardness. In using the preferred cement composition as a retrograde filling material, the water content is in the range of 10 to 40 weight percent, and most preferably three parts cement are used with one part water, or 25 weight % of the cement composition is water.

The fact that water is the principal reactant in the hardening reaction offers a significant advantage over many of the filling materials commonly used by allowing the cement to set in the moist environment of the body. Portland cement hardens by reactions with water, which are called hydration reactions. These reactions are complex, but principally involve the reaction of tricalcium silicate ($3CaO \cdot SiO_2$) and dicalcium silicate ($2CaO \cdot SiO_2$) with water. When these compounds react with water during the hardening of the cement, the principal hydration product is tricalcium silicate hydrate. This material is a colloidal gel of extremely small particles (less than 1 micron). The tricalcium silicate hardens rapidly and is most responsible for the early strength of Portland cement. The dicalcium silicate has a slower hydration reaction and is mainly responsible for strength increases beyond one week. Tricalcium aluminate, which plays a lesser role in the hardening process, hydrates rapidly also and contributes to early strength of development.

Portland cement is not radiopaque, but a radiopaque component may be added to render it radiopaque for purposes of dental diagnostics. Bismuth oxide ($Bi_2O_3$) has been found to be a suitable such compound. Depending on the degree of radiopaqueness desired, various ratios of additive may be used. In the preferred form of the cement composition, one part Bismuth oxide is used per four parts Portland cement. In addition, other additives or adjuvants could also be combined with the present cement composition to help facilitate and modify its beneficial therapeutic behavior. For example, small amounts of preservatives could be added, as well as stabilizers and desensitizers.

In many dental applications, the ultimate success of the treatment often depends on the adaption of the filling material to the tooth walls, and the resultant seal between the filler and the remaining tooth structure. An ideal seal will prevent the migration of bacteria and other byproducts into the cavity. The sufficiency of the seal is particularly important where the pulp chamber is to be sealed.

The clinician will recognize that adaption and sealing ability of a filling material can be measured in various ways. Any test of adaption and sealing ability attempts to determine the filling material's ability to seal the cavity from bacteria and other organisms that can promote further decay. Therefore, the filling material's effectiveness can also be directly determined by clinical studies; however, these are subject to many variables and require significant time and expense. To simulate the clinical function, the filling material can be evaluated by a dye penetration test.

Various dyes have been used to measure the sealing ability of materials to tooth structure, including the use of Rhodamine-B fluorescent dye as a tracer. A tandem scanning reflected light microscope ("SEM") is used to determine the degree of dye penetration.

This method of measuring the adaption and sealing ability is well known to the clinician. See, e.g., Tronstad, L., Trope, M., Doering, A. and Hasselgren, G. (1983), *Sealing Ability of Dental Amalgams as Retrograde Fillings and Endodontic Therapy*, J. Endodontics 9:551-53; Chung, B. S., Pitt Ford, J. R. and Watson, T. F. (1991) *The Adaptation and Sealing Ability of Light-Cured Glass Ionomer Retrograde Root Fillings*, Int'l Endodontic J. 24:223-32.

In dye penetration tests, the cavity is first prepared and filled with the material to be tested. This test allows a comparison, under controlled conditions, between the sealing ability of standard filling materials, such as amalgam, and the cement composition contemplated by the method of the present invention. After the outside of the tooth is coated to prevent dye leakage through anywhere but the cavity being tested, the tooth is immersed in a solution of the dye. The tooth is then sectioned and examined under the SEM, and the degree of dye leakage along cavity walls measured. Such leakage is expressed in terms of the distance (millimeters) travelled by the dye. In one such test, root canals for thirty single-rooted extracted human teeth were prepared using the standard step-back technique. The canals were obturated with gutta percha and Grossman sealer using the lateral condensation technique. The roots were then wrapped in moist gauze pads and kept in 100% humidity for a week prior to root end preparations.

Nail varnish was then applied to the entire external surface of each root and allowed to dry. About 3–4 millimeters of the apical segment of each root was removed at a 90° angle to the longitudinal axis of the root. The resected surface was acid etched, and a thin layer of pitting and fissure sealant was applied to prevent dye penetration through the exposed dentinal tubules.

The roots were then divided into three groups of ten, and the retrograde cavities were filled with one of the three retrograde filling materials: amalgam, EBA and the cement composition of the preferred embodiment. The roots were then placed in wet pieces of gauze and allowed to remain in 100% humidity for 24 hours. Next, the roots were totally immersed in an aqueous solution of Rhodamine B fluorescent dye for 24 hours.

By using a slow-speed diamond saw, each root was sectioned into two halves parallel to the longitudinal axis of the tooth. The extent of leakage along cavity walls was then observed under the SEM. The results, expressed in millimeters, are shown in Table I below.

TABLE I

Initial Leakage Dye Penetration Test Results: Highest Score of Fluorescent Dye Leakage (mm) Along Cavity Walls of Retrograde Filling.

| SAMPLE | AMALGAM | EBA | CEMENT COMPOSITION |
|--------|---------|-----|--------------------|
| 1 | 3 | 3 | 0 |
| 2 | 3 | 2 | 0 |
| 3 | 3 | 1 | 0 |
| 4 | 3 | 3 | <1* |
| 5 | 3 | 2 | 0 |
| 6 | 3 | 2 | 0 |
| 7 | 3 | 1 | <1 |
| 8 | 3 | 1 | <1 |
| 9 | 3 | 1 | 0 |
| 10 | 3 | 1 | <1 |

*Less than one-third of root end cavity depth.

Thus, in the case of retrograde cavities, the cement composition of the present invention performed significantly better than either amalgam or Super EBA cement. In various tests on retrograde fillings, amalgam allowed dye penetration all the way to the end of the retrograde cavity, which is typically 2-3 millimeters. Such cavities filled with Super EBA cement leaked less than those filled with amalgam, but significantly more than the cement composition of the present invention.

Thus, based on this dye penetration test and associated visualization, the cement composition associated with the present invention performs excellently as a filling and sealing material. Although direct extrapolation and relevance of such dye leakage studies to clinical practice has been questioned, such tests are the oldest and easiest method to test new restorative filling materials. Furthermore, when the filling material does not allow penetration of small molecules, such as those exhibited in the dye, it logically has the potential to prevent leakage of large molecules such as bacteria and/or by-products.

The adaption and sealing ability of a filling material can also be examined microscopically using the SEM to observe voids and gaps between the filling material and the tooth structure without the benefit of the dye leakage. When examined under the microscope, teeth filled with the preferred cement composition exhibited virtually no gaps or voids, and significantly less than that exhibited by either amalgam or Super EBA.

The application of the cement composition in filling and sealing teeth are numerous. The practitioner will realize that there are many suitable applications which fall within the method of the present invention. Examples are shown in FIGS. 1 through 7 and discussed below.

FIG. 1 shows an example of an anatomical structure with which the present invention may be used. FIG. 1 depicts a longitudinal section of a healthy single-rooted tooth 10 with pulp tissue 12, dentin 14 and enamel 16.

Figure 2:
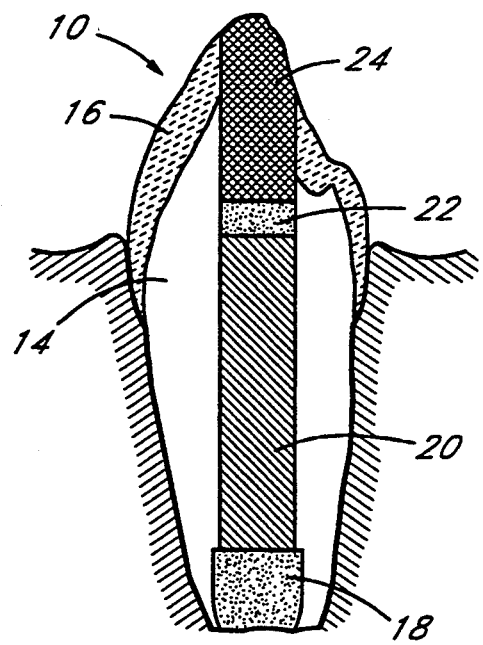
FIG. 2 is a longitudinal section of a single-rooted tooth after apicoectomy and retrograde filling with the Portland cement composition.

FIG. 2 depicts root canal therapy in a single-rooted tooth after apicoectomy and retrograde filling. The retrograde cavity 18 is shown filled with the cement composition. Substantially all of the remainder of the pulp chamber 20 is filled with standard obturating material such as gutta percha. In order to provide additional sealing, the pulp chamber may also be sealed at the coronal end 22 with the cement composition as shown in FIG. 2. The remainder of the tooth cavity is filled with a standard amalgam 24 or other permanent filling material.

The retrograde filling is performed in the standard manner, and the cement composition is applied using a suitable dental carrier. The preferred length of a filling or seal provided by the present cement composition is 2-3 mm, although other dimensions are possible. The incision may be closed upon completion of the retrograde filling, and the cement composition will harden sufficiently in vivo.

Prior to preparation of the cement composition, the Portland cement to be used therein may be sterilized, including gas sterilization, autoclaving or other suitable method.

When the cement composition is used as an orthograde cavity filler, as well as a pulp sealer, as shown in FIG. 2, the preferred method is to utilize a temporary filler for the remainder of the cavity 24 for twenty four hours to allow the cement composition to harden sufficiently. The temporary filling can then be replaced with the desired permanent filling material.

Figure 3:
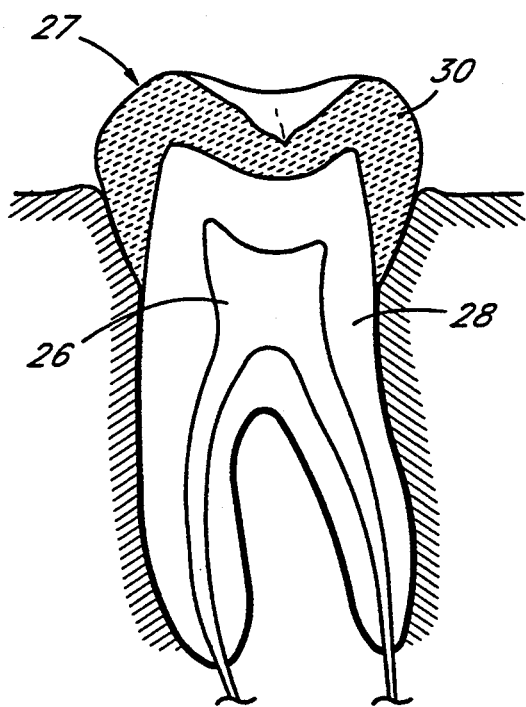
FIG. 3 is a longitudinal section of a healthy lower molar tooth showing two roots.

FIG. 3 is a further example of the environment in which the present invention may be used. FIG. 3 depicts a longitudinal section of a healthy lower molar tooth 27 with pulp tissue 26, dentin 28 and enamel 30.

Figure 4:
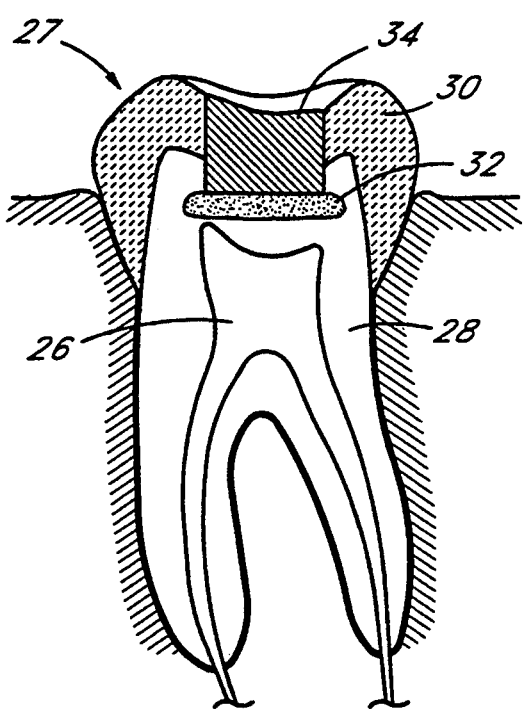
FIG. 4 is a longitudinal section of a molar tooth where decay has penetrated through the enamel and dentin. The Portland cement composition has been used as a base for a permanent filling material.

Use of the cement composition to seal a tooth where decay has penetrated through the enamel and dentin is shown in FIG. 4. The decay has been removed, and the cement composition has been used as a base 32 for a permanent filling 34 of any suitable material. Again, a temporary filling should be used for at least 24 hours to allow the cement to harden.

Figure 5:
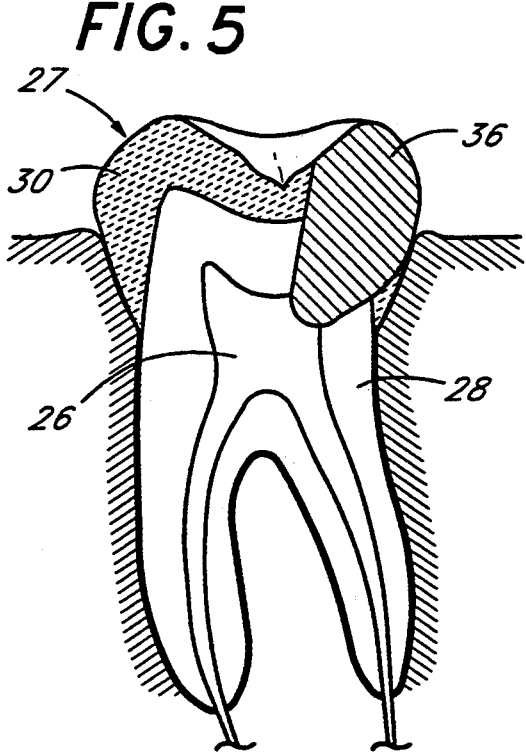
FIG. 5 shows a longitudinal section of a molar tooth where the decay has reached the pulp.
Figure 6:
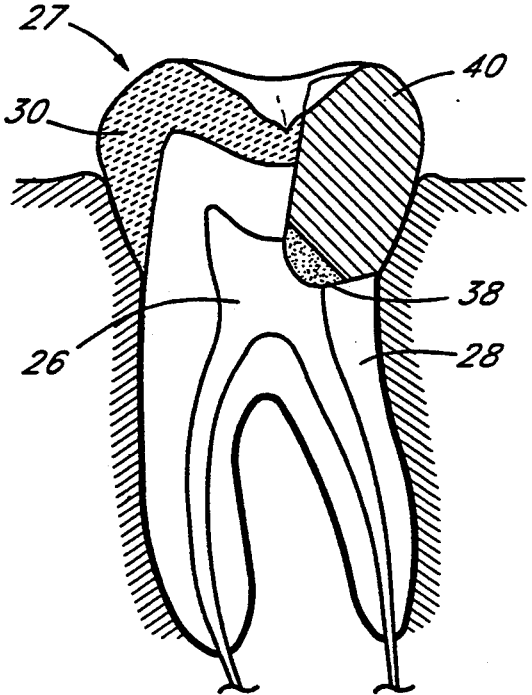
FIG. 6 is a longitudinal section of a molar tooth where decay has been removed and the pulp has been capped with Portland cement composition.

FIG. 5 shows a longitudinal section of a molar tooth 27 where the decay 36 has reached the pulp 26. Use of the Portland cement composition to seal a tooth where decay has reached the pulp is shown in FIG. 6. The decay 36 has been removed, and the Portland cement composition has been used to cap 38 the pulp 26, and the filling is completed with a permanent filling 40 of any suitable material.

Figure 7:
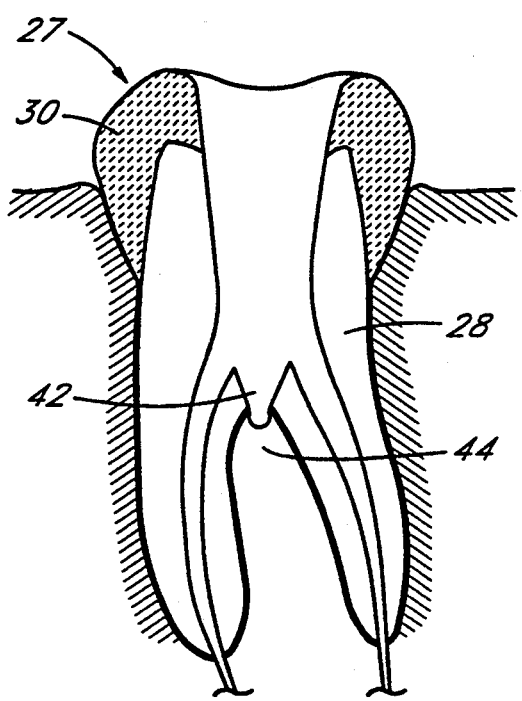
FIG. 7 is a longitudinal section of a molar tooth with a perforation in the furcation which has occurred during root canal therapy.
Figure 8:
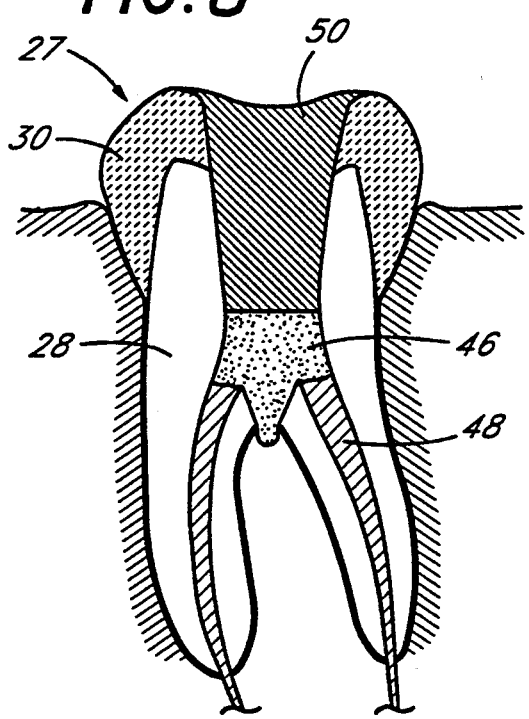
FIG. 8 is a molar tooth wherein the perforation of the furcation has been repaired with Portland cement composition after root canal therapy.

The Portland cement composition is also useful to repair any perforations which may occur during endodontic treatment. For example, FIG. 7 shows a perforation 42 in the furcation 44 which has occurred during root canal therapy. As seen in FIG. 8, the perforation 42 has been repaired with the present Portland cement composition 46 after root canal therapy. The remainder of the root canal therapy is standard wherein the canals have been obturated with gutta percha 48 or other suitable material, and the filling has been completed with a permanent filling material 50.

In conclusion, the present invention, through the use of the cement composition of the invention, embodies a novel method of filling and sealing human and veterinarian teeth. The described examples of how the dentist or endodontist can use the cement composition to seal teeth is illustrative, and not meant to be restrictive. The scope of the invention is, therefore, indicated by the claims rather than the foregoing description. Furthermore, the present invention may utilized in other specific forms without departing from its spirit or essential characteristics.

What is claimed is:

1. A method of sealing a tooth root canal in the course of an apicoectomy, comprising the steps of:
    (a) exposing the apex of a root of the tooth;
    (b) removing the apex of the root of the tooth whereby the root canal of the tooth is exposed;
    (c) preparing a root end cavity at the exposed root canal;
    (d) preparing a sealing material, comprising a cement having the following approximate composition:

| Component | Percentage |
| --- | --- |
| $SiO_2$ | 21% |
| $Al_2O_3$ | 4% |
| $Fe_2O_3$ | 5% |
| CaO | 65% |
| MgO | 2% |
| $SO_3$ | 2.5% |
| Alkalies ($Na_2O$, $K_2O$) | 0.5%; | and
    (e) introducing the sealing material into the root end cavity whereby the path of communication between the root canal and outer surface of the tooth is sealed.

2. The method of claim 1, wherein the cement has a Blaine number in the range of 4,000 to 5,500 $cm^2$/gram.

3. The method of claim 1, wherein the cement has a Blaine number in the range of 4,500 to 4,600 $cm^2$/gram.

4. The method of claim 1, wherein the sealing material is introduced into the root end cavity in the presence of water.

5. A method of filling a tooth cavity with a component capable of setting in an aqueous environment of the oral cavity of a mouth, comprising the steps of:
    (a) identifying the cavity of the tooth to be filled;
    (b) preparing a filling material, comprising a cement having the following approximate composition:

| Component | Percentage |
| --- | --- |
| $SiO_2$ | 21% |
| $Al_2O_3$ | 4% |
| $Fe_2O_3$ | 5% |

-continued

| Component | Percentage |
| --- | --- |
| CaO | 65% |
| MgO | 2% |
| $SO_3$ | 2.5% |
| Alkalies ($Na_2O$, $K_2O$) | 0.5%; | and (c) filling the tooth cavity with the filling material whereby said filling material seals the path of communication between the tooth cavity and the oral cavity of the mouth.

6. A method of performing an apicoectomy on a tooth comprising the steps of:
(a) removing the apex of a root of the tooth whereby the root canal of the tooth is exposed;
(b) preparing a root end cavity in the tooth;
(c) preparing a filling material, comprising a cement having the following approximate composition:

| Component | Percentage |
| --- | --- |
| $SiO_2$ | 21% |
| $Al_2O_3$ | 4% |
| $Fe_2O_3$ | 5% |
| CaO | 65% |
| MgO | 2% |
| $SO_3$ | 2.5% |
| Alkalies ($Na_2O$, $K_2O$) | 0.5%; | and p1 (d) filling the root end cavity with the filling material whereby the path of communication between the canal and the outer surface of the tooth is sealed.

7. The method of claim 6, wherein the cement has a Blaine number in the range of 4,000 to 5,500 $cm^2$/gram.

8. The method of claim 6, wherein the cement has a Blaine number in the range of 4,500 to 4,600 $cm^2$/gram.

9. The method of claim 6, wherein the root end cavity is filled in the presence of water.

10. A method of sealing a root perforation which has created a path of communication between a canal of the tooth and an outer surface of the tooth, said method comprising the steps of:
(a) identifying the root perforation;
(b) preparing the root perforation for placement of a filling material therein;
(c) preparing a filling material, comprising a cement having the following approximate composition:

| Component | Percentage |
| --- | --- |
| $SiO_2$ | 21% |
| $Al_2O_3$ | 4% |
| $Fe_2O_3$ | 5% |
| CaO | 65% |
| MgO | 2% |
| $SO_3$ | 2.5% |
| Alkalies ($Na_2O$, $K_2O$) | 0.5%; | and
(d) filling the root perforation with the filling material whereby said filling material seals the path of communication between the outer surface of the tooth and the canal of the tooth.

* * * * *